United States Patent [19]

Schrider

[11] 4,078,080

[45] Mar. 7, 1978

[54] ORAL ADMINISTRATION OF PYRETHROIDS TO WARM-BLOODED ANIMALS TO PREVENT FLY DEVELOPMENT IN THEIR DROPPINGS

[75] Inventor: Michael Stanley Schrider, South Bound Brook, N.J.

[73] Assignee: American Cyanamid Company, Stamford, Conn.

[21] Appl. No.: 750,088

[22] Filed: Dec. 13, 1976

[51] Int. Cl.² ............................................... A01N 9/20
[52] U.S. Cl. .................................... 424/304; 424/305; 424/306; 424/308
[58] Field of Search ........................ 424/304, 305, 308

[56] References Cited

U.S. PATENT DOCUMENTS

| 3,962,458 | 6/1976 | Schrider | 424/304 |
| 3,966,959 | 6/1976 | Addor | 424/304 |

*Primary Examiner*—Leonard Schenkman
*Attorney, Agent, or Firm*—H. G. Jackson

[57] ABSTRACT

The invention is a novel method for the control of flies breeding in manure, comprising orally administering certain pyrethroids to warm-blooded animals to provide pesticidally effective amounts of these pyrethroids in the feces of the animals. The invention includes animal feed compositions, comprising a mixture of a nutritionally balanced feed and a pyrethroid, incorporated in the feed to provide pesticidally effective amounts of the pyrethroid in the feces of the animals.

6 Claims, No Drawings

ORAL ADMINISTRATION OF PYRETHROIDS TO WARM-BLOODED ANIMALS TO PREVENT FLY DEVELOPMENT IN THEIR DROPPINGS

Flies breeding in manure and feces of warm-blooded animals are common pests of the animals. Uncontrolled, and in large numbers they irritate and distress these animals to a degree that the animals become restless, hyperactive, and may even stop feeding temporarily. The net result is that the distressed animals will lose weight. Additionally, these flies are also vectors in the dissemination of a number of diseases, animals (and man) are subject to. Thus, the control of flies is highly desirable, especially where large numbers of warm-blooded animals are kept, such as on farms, feedlots, shipping yards and the like.

U.S. Pat. No. 3,966,959 (1976) teaches the phenoxybenzyl esters of spirocarboxylic acids useful in the invention and their use as insecticides. U.S. Pat. No. 3,962,458 (1976) teaches systemic control of ectoparasites with the compounds useful in the invention.

Flies, such as stable flies (*Stomoxys calcitrans*), horn flies (*Siphona irritans*), house flies (*Musca domestica*), face flies (*Musca autumnalis*) and other flies which breed in manure are common pests of ward-blooded animals such as cattle, horses, sheep, goats, swine and poultry. These flies may, especially in large numbers, irritate, annoy and otherwise cause great distress among the animals to such an extent that the animals may stop feeding and become restless with the net result that the animals will lose rather than gain weight. The weight loss thus incurred is substantial on a world-wide basis, and the corresponding financial losses are considerable. Additionally, it is well-known that flies are also vectors in the dissemination of certain diseases of the animals and diseases of man. Thus, control of the flies is highly desirable.

Customarily, to control flies, in barns and other animal shelters, the animals themselves, and their environment in general, are treated with pesticides. Though usually effective, these methods of control are time consuming and expensive. Moreover, it is generally very difficult if not impossible to effectively treat animal feces and manure with pesticides to prevent the flies from breeding therein.

Surprisingly, I have found, that by the novel method of the invention, satisfactory fly control may be achieved, as described below.

Pyrethroids, represented by formula (I):

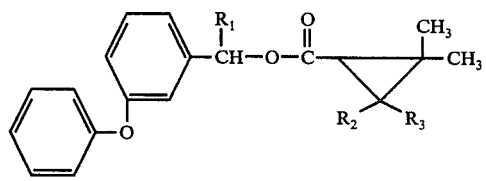

wherein $R_1$ is hydrogen or cyano; $R_2$ and $R_3$ together with the carbon atom to which they are attached represent a cyclic moiety selected from

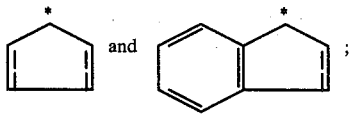

wherein the carbon atom of the cyclic moiety marked with an asterisk is shared with the cyclopropane ring, and wherein ==== represents a single or double bond; when administered orally to provide pesticidally effective amounts in the feces of warm-blooded animals such as cattle, horses, sheep, goats, swine and poultry will pass rapidly through the animals alimentary canal, and will ultimately appear in the feces of the animals.

Larvae of the above-identified flies, developing in, and feeding on manure containing the pyrethroids of formula (I) in pesticidally effective amounts, will either fail to pupate or to develop from the pupae into mature flies.

For oral administration, the above-identified pyrethroids may be formulated as pills, tablets, boluses and the like to provide a daily dosage of 0.1 mg to 5.0 mg/kg body weight of the compounds. Advantageously, the pyrethroids may also be administered in, or with the animals feed (or drinking water) in amounts of 10 ppm to 500 ppm and preferably 25 ppm to 250 ppm by weight of feed; or in amounts corresponding to 0.1 mg to 5.0 mg/kg body weight of the animals.

The thus administered pyrethroids will rapidly pass through the animals alimentary canal, and will equally rapidly appear in pesticidally effective amounts in the feces of the animals. Consequently, fly larvae developing in, and feeding on the thus medicated feces (manure) can be controlled effectively with the compounds.

It is recognized of course, that by the hereinabove described method, the pyrethroids may not give the same degree of control for all of the fly species, nevertheless the use of the pyrethroids for the control of flies is novel and hitherto undisclosed.

The invention is further illustrated by the nonlimiting examples set forth below.

EXAMPLE 1

In vitro evaluation of pyrethroids as potential feed additives for fly control

A solution of the compound under test is prepared by dissolving 100 mg of pyrethroid in acetone and adjusting the volume of the solution to 100 ml with acetone. One and 10 ml aliquots of the solution are added to 1 kg each of fresh cow manure and mixed for 1 minute with an electric mixer. manure used for unmedicated controls is processed the same way, except only acetone is added. The manure samples are divided between 4 paper souffle cups. At each level of concentration (and of controls) two cups are seeded with day-old face fly larvae and two with day-old house fly larvae. The cups are held for 7 days at about 80° F and 50% r.h. The cups are then examined for pupae, which are counted, weighed and placed in plastic vials to emerge and die. After the flies are dead, they are counted and percentages calculated. The data obtained are summarized in Table I below.

Table I

In Vitro Evaluation of Pyrethroids as Potential Feed Additives for the Control of Flies in Manure, at One and 10 ppm Level; Data are Averages of Two Replicates

| Compound | Concentration in Manure ppm | Face Flies % Larvae Reaching Pupal Stage | Face Flies % Adult Eclosion from Pupae | House Flies % Larvae Reaching Pupal Stage | House Flies % Adult Eclosion from Pupae |
|---|---|---|---|---|---|
| Control | 0 | 80 | 22 | 86 | 95 |
| 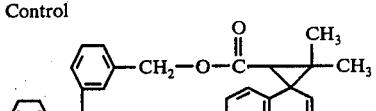 | 1 | 74 | 22 | 86 | 95 |
|  | 10 | 0 | — | 22 | 82 |
| spiro[cyclopropane-1,1'-indene]-2-carboxylic acid, 3,3-dimethyl-, 3-phenoxybenzyl ester. | | | | | |
| 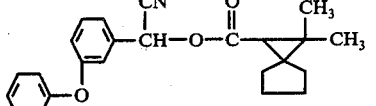 | 1 | 30 | 7 | 76 | 92 |
|  | 10 | 0 | — | 0 | — |
| spiro[2.4]heptane-1-carboxylic acid, 2,2-dimethyl-, α-cyano-3-phenoxybenzyl ester. | | | | | |
| Control | 0 | 80 | 45 | 86 | 91 |
| 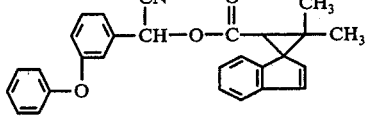 | 1 | 64 | 44 | 88 | 93 |
|  | 10 | 0 | — | 0 | — |
| spiro[cyclopropane-1,1'-indene]-2-carboxylic acid, 3,3-dimethyl-, α-cyano-3-phenoxybenzyl ester. | | | | | |

EXAMPLE 2

In vitro evaluation of pyrethroids as potential feed additives for the control of flies A 10 mg sample of the compound under test is dissolved in acetone and the volume of the solution adjusted to 100 ml with acetone. A 10 ml aliquot of the above solution is added to 1 kg of fresh, unmedicated cow manure and mixed for 3 minutes with a hobart heavy duty mixer.

After thorough mixing, 2 samples of about 400 g each are placed in sweetheart plastic 4 oz cups and seeded with 20 two-day old *Musca autumnalis* larvae. The larvae are allowed to feed in the manure and pupate. They are then collected, counted and compared to control groups. The data obtained are summarized in Table II below.

EXAMPLE 3

In vivo evaluation of pyrethroids as potential feed additives for the control the flies in manure One 192 kg Hereford-Angus crossbred steer is fed 1 mg/kg body weight of the compound under test for seven consecutive days to measure face fly control in manure. Feces are collected for three days before treatment (to establish untreated control counts), seven days during treatment, and nine days posttreatment (to allow time for most of the compound to pass through the animal and establish pupal recovery counts near the pretreatment counts).

Samples of the feces are placed daily in three 5 oz plastic cups and seeded with 20 two-day old *Musca autumnalis* larvae.

For the seven day period, beginning one day after treatment, an average of 99.3 percent mortality of face fly larvae is observed when compared to pretreatment counts. A gradual increase in recovered pupae occurs during the posttreatment period.

I claim:

1. A method for the control of development of flies in the manure of warm-blooded animals, comprising administering to the animals orally, a compound of formula:

Table II

In vitro Evaluation of a Pyrethroid as a Potential Feed Additive for the Control of Flies in Manure at one ppm Level; Two Replicates

| Compound | Concentration in Manure ppm | Musca autumnalis No. of Larvae Added | Musca autumnalis No. of Pupae Found |
|---|---|---|---|
| Control | 0 | 20 | 13 |
| Control | 0 | 20 | 15 |
| 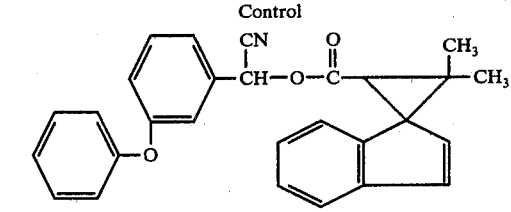 | 1 | 20 | 0 |
|  | 1 | 20 | 0 |

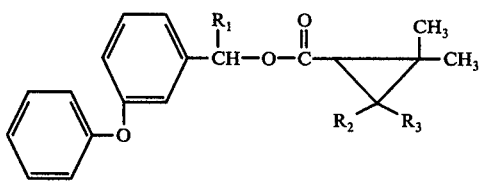

wherein $R_1$ is hydrogen or cyano; $R_2$ and $R_3$ together with the carbon atom to which they are attached represent a cyclic moiety of

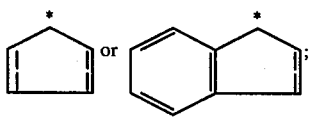

wherein the carbon atom of the cyclic moiety marked with an asterisk is shared with the cyclopropane ring, and wherein ═══ represents a single or double bond; in amounts corresponding to 0.1 mg. to 5.0 mg/kg body weight of the annimals.

2. A method according to claim 1, wherein the compound is spiro[cyclopropane-1,1'-indene]-2-carboxylic acid, 3,3-dimethyl-, 3-phenoxybenzyl ester.

3. A method according to claim 1, wherein the compound is spiro[cyclopropane-1,1'-indene]-2-carboxylic acid, 3,3-dimethyl-, α-cyano-3-phenoxybenzyl ester.

4. A method according to claim 1, wherein the compound is spiro[2.4]heptane-1-carboxylic acid, 2,2-dimethyl-, α-cyano-3-phenoxybenzyl ester.

5. A method according to claim 1, wherein the animals are cattle, horses, sheep, goats, swine and poultry.

6. A method according to claim 1, wherein the flies are stable flies, horn flies, house flies and face flies.

* * * * *